(12) United States Patent
Cho et al.

(10) Patent No.: US 11,712,414 B2
(45) Date of Patent: *Aug. 1, 2023

(54) ORAL PHARMACEUTICAL COMPOSITION FOR PREVENTING OR TREATING DRY EYE SYNDROME COMPRISING REBAMIPIDE OR A PRODRUG THEREOF

(71) Applicants: SAMJIN PHARMACEUTICAL CO., LTD., Seoul (KR); ASTECH. CO., LTD., Suwon-si (KR)

(72) Inventors: Eui Hwan Cho, Seoul (KR); Sung Ju Choi, Seoul (KR); Sung Woo Lee, Seoul (KR); Hee Jong Shin, Bucheon-si (KR); Jong Bae Yoon, Suwon-si (KR); Ki Seok Park, Siheung-si (KR); Ho Tae Nam, Suwon-si (KR)

(73) Assignees: SAMJIN PHARMACEUTICAL CO., LTD., Seoul (KR); ASTECH. CO., LTD., Gyeonggi-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/784,956

(22) PCT Filed: Apr. 17, 2014

(86) PCT No.: PCT/KR2014/003329
§ 371 (c)(1),
(2) Date: Oct. 16, 2015

(87) PCT Pub. No.: WO2014/171748
PCT Pub. Date: Oct. 23, 2014

(65) Prior Publication Data
US 2016/0081922 A1    Mar. 24, 2016

(30) Foreign Application Priority Data
Apr. 18, 2013  (KR) .......................... 10-2013-0043141

(51) Int. Cl.
| | |
|---|---|
| *A61K 31/5377* | (2006.01) |
| *A61K 31/4704* | (2006.01) |
| *A61P 27/00* | (2006.01) |
| *A61K 31/4725* | (2006.01) |
| *A61K 9/00* | (2006.01) |
| *A61K 31/496* | (2006.01) |

(52) U.S. Cl.
CPC ........ *A61K 9/0053* (2013.01); *A61K 31/4704* (2013.01); *A61K 31/496* (2013.01); *A61K 31/5377* (2013.01)

(58) Field of Classification Search
CPC .............. A61K 31/4704; A61K 31/496; A61K 31/5377; A61K 9/0053; A61P 27/00; A61P 27/02
USPC ............................................ 514/235.2, 236.2
See application file for complete search history.

(56) References Cited

U.S. PATENT DOCUMENTS

| | | | |
|---|---|---|---|
| 6,060,486 A | 5/2000 | Urashima et al. | |
| 7,589,109 B2* | 9/2009 | Uchida | ................... A61P 25/00 514/323 |
| 9,211,254 B2* | 12/2015 | Matsuda | .................. A61P 31/04 |
| 9,447,077 B2* | 9/2016 | Burnier | .................. A61K 45/06 |
| 2007/0287729 A1 | 12/2007 | Matsuda et al. | |
| 2009/0258069 A1* | 10/2009 | Burnier | ..................... A61P 1/00 424/722 |
| 2011/0124682 A1 | 5/2011 | Sumida et al. | |
| 2015/0141409 A1* | 5/2015 | Cho | ................... A61K 31/4704 514/217.07 |
| 2015/0218135 A1* | 8/2015 | Burnier | ................... A61P 17/14 514/307 |
| 2016/0081922 A1* | 3/2016 | Cho | ..................... A61K 31/496 514/235.2 |

FOREIGN PATENT DOCUMENTS

| | | | | |
|---|---|---|---|---|
| EP | 2285413 | | 8/2012 | |
| EP | 2865669 B1 * | | 4/2021 | ............. A61P 19/02 |
| JP | 09301866 A | | 11/1997 | |
| KR | 10-2011-0027786 A | | 3/2011 | |
| WO | 97-13515 A1 | | 4/1997 | |
| WO | 2008-074853 A1 | | 6/2008 | |

OTHER PUBLICATIONS

Phase III Study REsults for REbamipide Ophthalmic Suspension for Dry Eye Announced at ARVO 2011, Tokyo, Japan, May 6, 2011—Otsuka Pharmaceutical Co., Ltd., ARVO* 2011 (May 1 -5, 2011, Fort Lauderdale, Florida, USA).*

Kinoshita et al. (A Randomized, Multicenter Phase 3 Study comparing 2% Rebamipide (OPC-12759) with 0.1% Sodium Hyaluronate in the Treatment of Dry Eye, Ophthalomology 2013;120:1158-1165).*

Beaumont et al. (Curr. Drug Metab. (Dec. 2003. 4(6), 461-85, abstract).*

(Continued)

*Primary Examiner* — Samira J Jean-Louis
(74) *Attorney, Agent, or Firm* — Cantor Colburn LLP

(57) ABSTRACT

Disclosed is an oral pharmaceutical composition for preventing or treating dry eye syndrome, which comprises rebamipide or a prodrug thereof, or a pharmaceutically acceptable salt thereof, as an active ingredient. The compounds can treat dry eye syndrome via oral route, and can be thus employed safely and conveniently compared to conventional eye drops.

11 Claims, 15 Drawing Sheets

(56) References Cited

OTHER PUBLICATIONS

Jana et al. (Current Medicinal Chemistry, vol. 17, No. 32,pp. 3874-3908(35), publication date Nov. 1, 2010, abstract).*
Shin, Boom Soo et al. (Drug Development and Industrial Pharmacy, vol. 30, No. 8. pp. 869-876, 2004).*
Helieh S. Oz et al. (Molecules 2008. 13. 452-474).*
Japanese Office Action—Japanese Application No. 2016-508869 dated Jul. 22, 2016, citing JP 09-301866, JP 2011-524854, WO 2008/074853, and JP 2015-522585.
International Search Report for PCT/KR2014/003329 dated Aug. 26, 2014 from Korean Intellectual Property Office.
Kinoshita, S. et al., "Rebamipide.(OPC-12759) in the treatment of dry eye: a randomized, double-masked, multicenter, placebo-controlled phase II study", Ophthalmology, 2012, vol. 119, No. 12, pp. 2471-2478.
Kohashi, Masayuki et al., "Effective treatment with oral administration of rebamipide in a mouse model of Sjgren's syndrome", Arthritis & Rheumatism, 2008, vol. 58, No. 2, pp. 389-400.

* cited by examiner

ORAL PHARMACEUTICAL COMPOSITION FOR PREVENTING OR TREATING DRY EYE SYNDROME COMPRISING REBAMIPIDE OR A PRODRUG THEREOF

CROSS REFERENCE TO PRIOR APPLICATIONS

This application is a National Stage Application of PCT International Patent Application No. PCT/KR2014/003329 filed on Apr. 17, 2014, under 35 U.S.C. § 371, which claims priority to Korean Patent Application No. 10-2013-0043141 filed on Apr. 18, 2013, which are all hereby incorporated by reference in their entirety.

TECHNICAL FIELD

The present invention relates to an oral pharmaceutical composition for preventing or treating dry eye syndrome, which comprises rebamipide or a prodrug thereof.

BACKGROUND ART

Dry eye syndrome is a clinical condition characterized by deficient tear production caused by lacrimal gland inflammation and corneal denervation or by excessive tear evaporation caused by meibomian gland dysfunction or eyelid disorders. Further, T-cell-mediated inflammatory responses were reported responsible for the pathogenesis of dry eye syndrome (*Eye Contact Lens*, 29(1 Suppl):S96-100, 2003; and *Opthalmologe*, 103:9-17, 2006).

Symptoms of dry eye syndrome involve burning, foreign-body sensation, itching, redness, and in severe cases impaired vision. Dry eye syndrome was recognized as a characteristic sign of aging which is common among women of post-menopausal age. But, with recent increases in TV watching, use of computers, and wearing of contact lens, this condition becomes frequent in both men and women. Further, the onset age of dry eye syndrome is gradually decreasing (*Gynecol. Endocrinol.*, 20:289-98, 2005; and *Surv. Opthalmol.*, 50:253-62, 2005).

Approaches for the treatment of dry eye syndrome include instillation of artificial tears for artificial tear supplementation, instillation of steroidal anti-inflammatory eye drops to inhibit inflammatory responses, therapeutic contact lens (TCL) wear, surgical occlusion of the punctum to suppress tear escape from one's eye to result in prolonged ocular retention of artificial tear solutions or substitutes, and the like (*J. Korean Opthalmol. Soc.*, 46:1774-1779, 2005). However, there are disadvantages that artificial tear preparations should be applied several times a day due to their temporary effects and have no protective effects against corneal damage, and that steroid preparations may cause fatal side effects such as glaucoma upon chronic administration. In addition, therapeutic contact lens are inconvenient to wear, and may also be a potential source of bacterial infections. Further, the punctual occlusion has disadvantages such as mental rejection feelings due to the surgical operation, and difficulty to restore the former state upon the occurrence of adverse side effects. Above all, the aforementioned conventional remedies are merely symptomatic therapies, which are not focused to treat or address the root causes of dry eye conditions.

In 2006, an eye drop for the treatment of dry eye syndrome using the immunomodulator cyclosporine, also called Restasis®, was developed by Allergan Incorporation in the United States. Restasis eye drops have been reported to inhibit the production and activation of immunocytes associated with keratoconjunctivitis sicca and to increase the tear secretion level (*Opthalmology*, 107:967-74, 2000; and *Opthalmology*, 107:631-9, 2000). However, the preparation exerts drug efficacy thereof via anti-inflammatory action, thus requiring repeated drug administrations for several months enough to achieve satisfactory therapeutic effects. Further, its administration is accompanied by relatively high frequency of occurrence (17%) of a typical side effect, e.g. burning sensation (*Opthalmology*, 107:631-9, 2000; and Thomson Pharma).

Therefore, there still remains a need for development of a therapeutic agent which is not a symptomatic therapeutic merely palliating symptoms and is capable of treating the root causes of dry eye syndrome while securing safety of drug medications due to low manifestation of adverse side effects.

Rebamipide, 2-(4-chlorobenzoyl-amino)-3-[2(1H)-quinolon-4-yl]propionic acid represented by Chemical Formula I, is known as a useful therapeutic of gastric ulcer. Further, rebamipide has an Increasing action of goblet cell density in eye, and an increasing action of lacrimal fluid, and has been already known as an agent for treating dry eye syndrome (JP-A-2009-301866).

<Chemical Formula I>

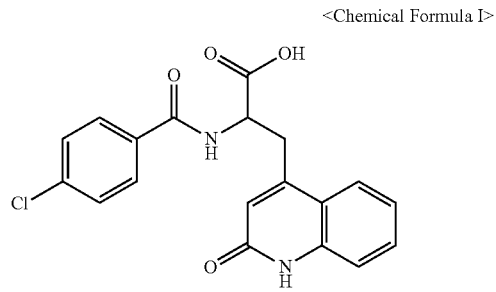 [SMILES: O=C(NC(Cc1cc(=O)[nH]c2ccccc12)C(=O)O)c1ccc(Cl)cc1]

Regarding treatment for dry eye syndrome, US publication No. 2007-0287729 discloses an ophthalmic product containing rebamipide of neutral to weakly acidic pH, more particular, an aqueous suspension of crystalline rebamipide which comprises a mixture of at least one of the compounds selected from water-soluble polymers and surfactants, an aqueous acidic solution, and an aqueous solution containing a water-soluble salt of rebamipide. Further, KR publication No. 10-2011-0027786 describes an ophthalmic pharmaceutical composition containing rebamipide, amino sugars and buffers, exclusive of inorganic cations.

However, as the aforementioned compositions are in the form of eye drops for the treatment of dry eye syndrome, they tend to stimulate eye mucosa topically, are difficult to be administered in a fixed dose, have short shelf lives, and have poor compliances, resulting in significant low therapeutic efficacies.

DISCLOSURE

Technical Problem

It is an object of the present invention to provide a pharmaceutical composition containing rebamipide, which can prevent or treat dry eye syndrome via oral route, not via ocular route.

Technical Solution

In accordance with an aspect thereof, the present invention provides an oral pharmaceutical composition for preventing or treating dry eye syndrome, which comprises rebamipide or a prodrug thereof, or a pharmaceutically acceptable salt thereof, as an active ingredient.

Advantageous Effects

As descried hitherto, rebamipide or a prodrug thereof, or a pharmaceutically acceptable salt thereof can treat dry eye syndrome via oral route, and can be thus employed safely and conveniently compared to conventional eye drops.

MODE FOR INVENTION

Figure 1:
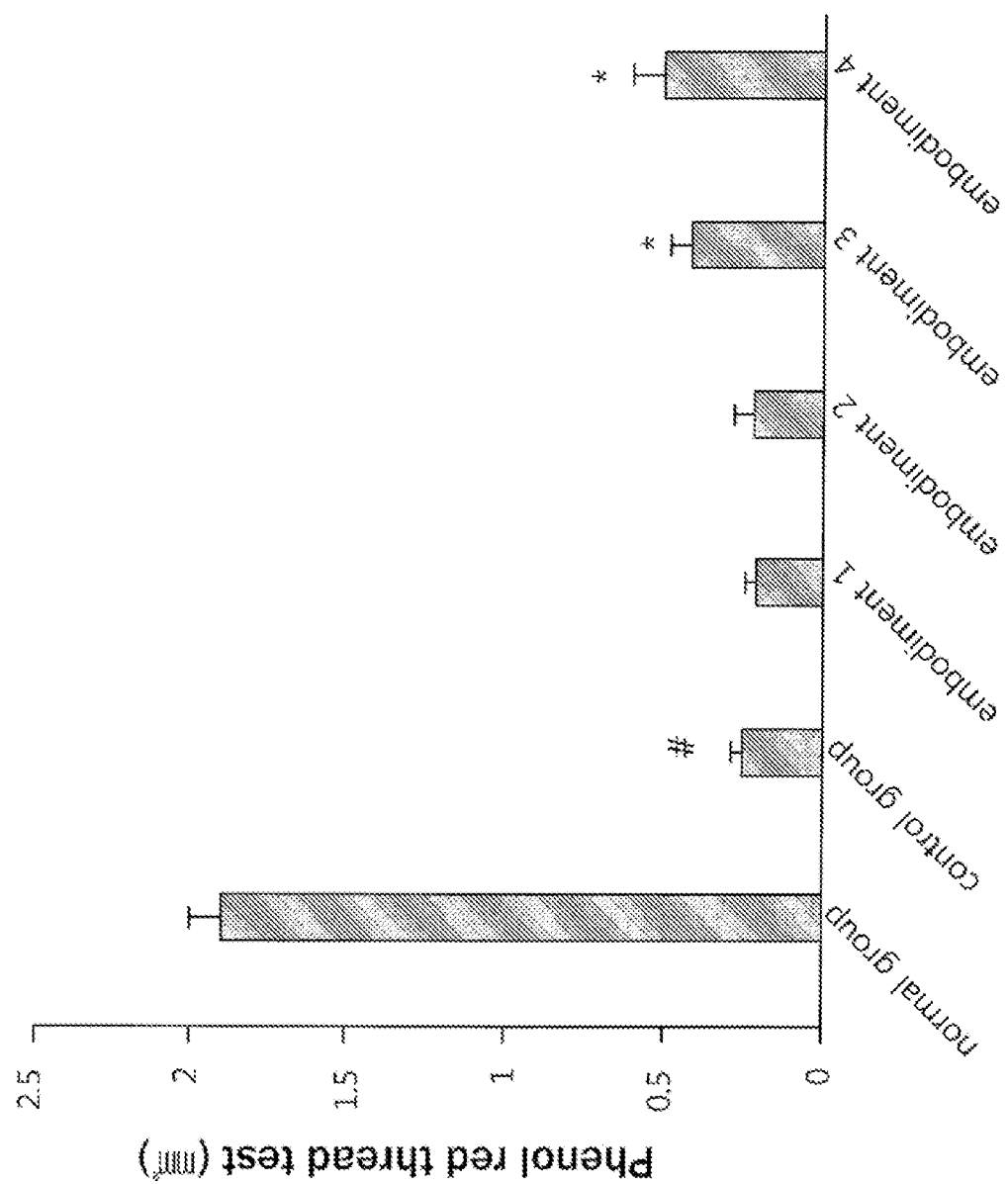
FIGS. 1 to 5 are graphs showing tear production volumes in mouse models of dry eye syndrome at 10 days after administration of the oral compositions according to the present invention (Examples 1 to 28). In the graphs, "normal group" refers to mice with no dry eye syndrome induced, and "control group," to dry eye syndrome mouse models administered with vehicle only. Also, symbol "#" indicates $p<0.05$ against the normal group, and "*" indicates $p<0.05$ against the control group (t-test).

A detailed description will be given of the present invention, below.

In accordance with an aspect thereof, the present invention provides an oral pharmaceutical composition for preventing or treating dry eye syndrome, which comprises rebamipide or a prodrug thereof, or a pharmaceutically acceptable salt thereof, as an active ingredient.

Rebamipide, represented by Chemical Formula I, is known as a therapeutic for gastric ulcer or dry eye syndrome:

[Chemical Formula I]

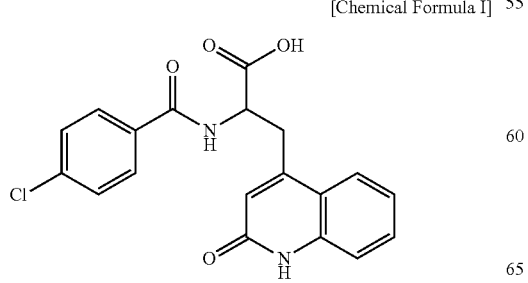

In particular, regarding dry eye syndrome, rebamipide has been used only in the form of eye drops, which was considered to be most effective, as the formulation can deliver drugs and additional moisture directly to eye.

However, the present invention suggests extraordinary findings that rebamipide, even upon oral administration, stimulates mucous secretion in the conjunctiva and inhibits ocular surface damages, thereby exhibiting superior therapeutic effects on dry eye syndrome. Usually, eye drops and orally administered agents cannot exhibit same efficacy due to different mechanisms of action between them, although same drugs are comprised. In particular, considering that an orally administered agent tends to degrade during its passage through various organs in body and takes substantial times to reach a target site, it is not sure whether the orally administered agent has comparable effects to eye drops. Nevertheless, the present inventors have revealed that rebamipide administered via oral route exhibits therapeutic effects on dry eye syndrome. Therefore, the agent for oral administration of the present invention may be employed in lieu of eye drops having problems of possibility to evoke irritation, difficulty of administration in a fixed dose, low compliance and short shelf-life.

The inventive composition may comprise a rebamipide prodrug or a pharmaceutically acceptable salt thereof, instead of rebamipide.

The rebamipide prodrug refers to a compound which can degrade into rebamipide in vivo, and particularly to a compound having a group which can be easily split off from the compound after absorption in vivo. The prodrug is used to increase the absorption in vivo or enhance the solubility.

Preferred examples of the prodrug may include the compounds of the following Chemical Formulae II to VII:

[Chemical Formula II]

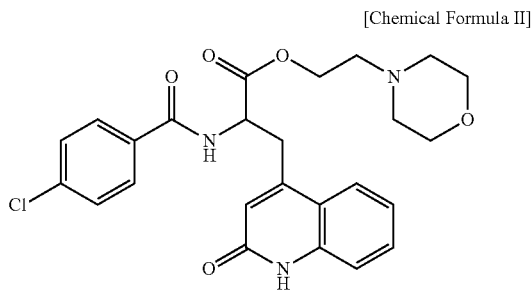 [SMILES: O=C(NC(Cc1cc(=O)[nH]c2ccccc12)C(=O)OCCN1CCOCC1)c1ccc(Cl)cc1]

The compound of Chemical Formula II, (2-morpholinoethyl 2-(4-chlorobenzamido)-3-(2-oxo-1,2-dihydroquinolin-4-yl)propanoate, is used interchangeably with 'rebamipide prodrug I.' The rebamipide prodrug I may be prepared by reacting rebamipide with 4-(2-hydroxyethyl)morpholine.

[Chemical Formula III]

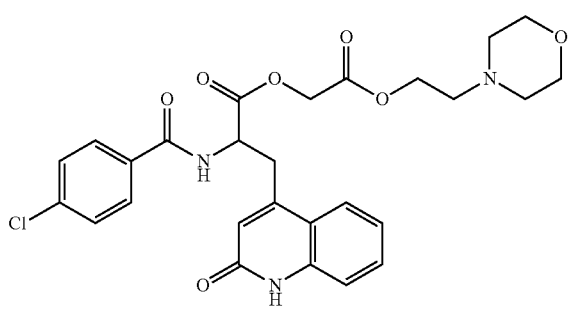

The compound of Chemical Formula III, (2-morpholinoethoxy)-2-oxoethyl 2-(4-chlorobenzamido)-3-(2-oxo-1,2-dihydroquinolin-4-yl)propanoate, is used interchangeably with 'rebamipide prodrug II.' The rebamipide prodrug II may be prepared by reacting rebamipide with 4-(2-(2-bromoacetoxy)ethyl) morpholin-4-ium bromide.

[Chemical Formula IV]

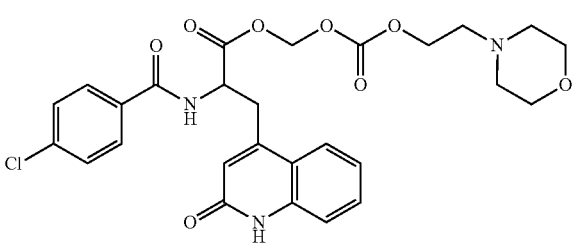

The compound of Chemical Formula IV, ((2-morpholinoethoxy)carbonyloxy)methyl 2-(4-chlorobenzamido)-3-(2-oxo-1,2-dihydroquinolin-4-yl)propanoate, is used interchangeably with 'rebamipide prodrug III.' The rebamipide prodrug III may be prepared by reacting rebamipide with 4-(2-(3-chloropropanoyloxy)ethyl)morpholin-4-ium bromide.

[Chemical Formula V]

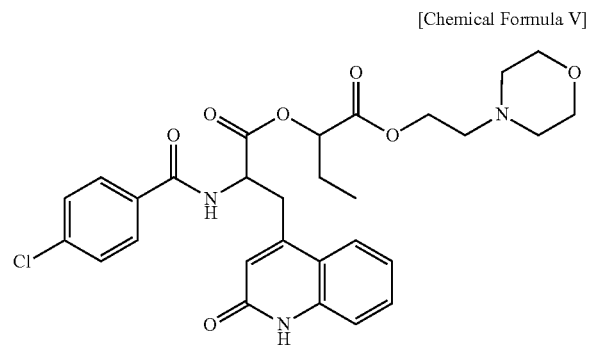 [SMILES: CCC(OC(=O)C(Cc1cc(=O)[nH]c2ccccc12)NC(=O)c1ccc(Cl)cc1)C(=O)OCCN1CCOCC1]

The compound of Chemical Formula V, 2-morpholinoethyl 2-(2-(4-chlorobenzamido)-3-(2-oxo-1,2-dihydroquinolin-4-yl)propanoyloxy)-butanoate, is used interchangeably with 'rebamipide prodrug IV.' The rebamipide prodrug IV may be prepared by reacting rebamipide with 4-(2-(2-bromobutanoyloxy)ethyl)morpholin-4-ium.

[Chemical Formula VI]

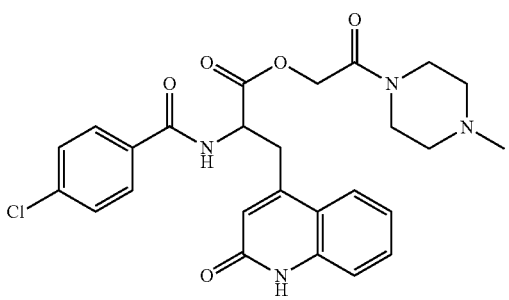

The compound of Chemical Formula VI, (2-(4-methylpiperazin-1-yl)-2-oxoethyl 2-(4-chlorobenzamido)-3-(2-oxo-1,2-dihydroquinolin-4-yl)propanoate, is used interchangeably with 'rebamipide prodrug V.' The rebamipide prodrug V may be prepared by reacting rebamipide with 1-(2-bromoacetyl)-4-methylpiperazin-1-ium.

[Chemical Formula VII]

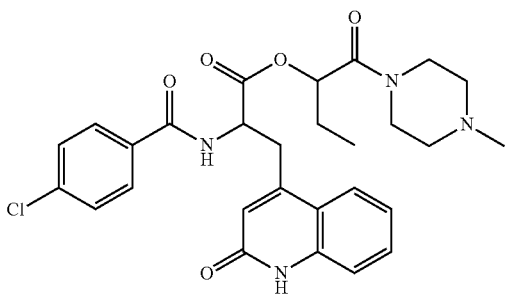

The compound of Chemical Formula VII, 1-(4-methylpiperazin-1-yl)-1-oxobutan-2-yl 2-(4-chlorobenzamido)-3-(2-oxo-1,2-dihydroquinolin-4-yl)propanoate, is used interchangeably with 'rebamipide prodrug VI.' The rebamipide prodrug VI may be prepared by reacting rebamipide with 1-(2-bromobutanoyl)-4-methylpiperazin-1-ium bromide.

Figure 2:
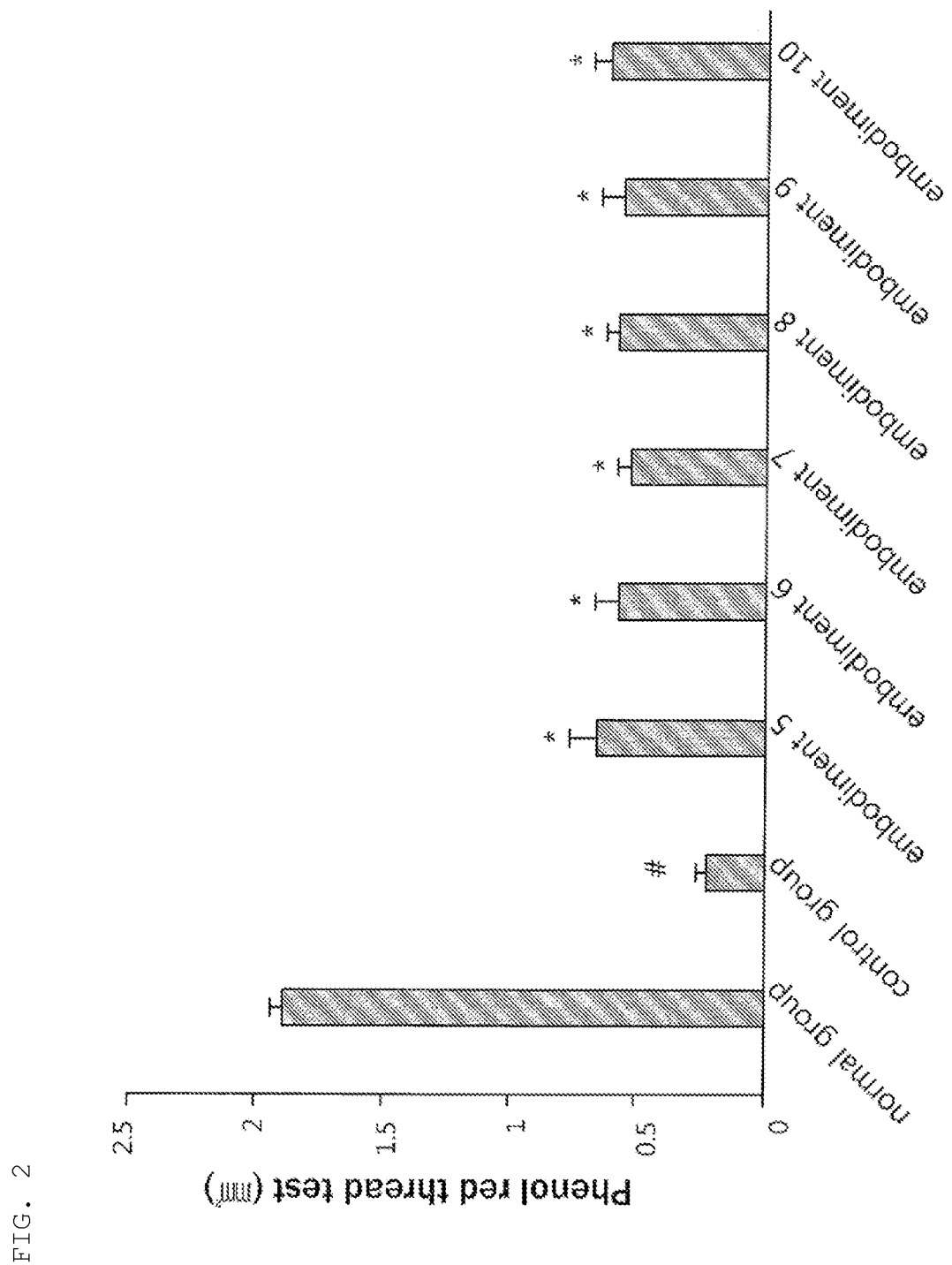
Figure 3:
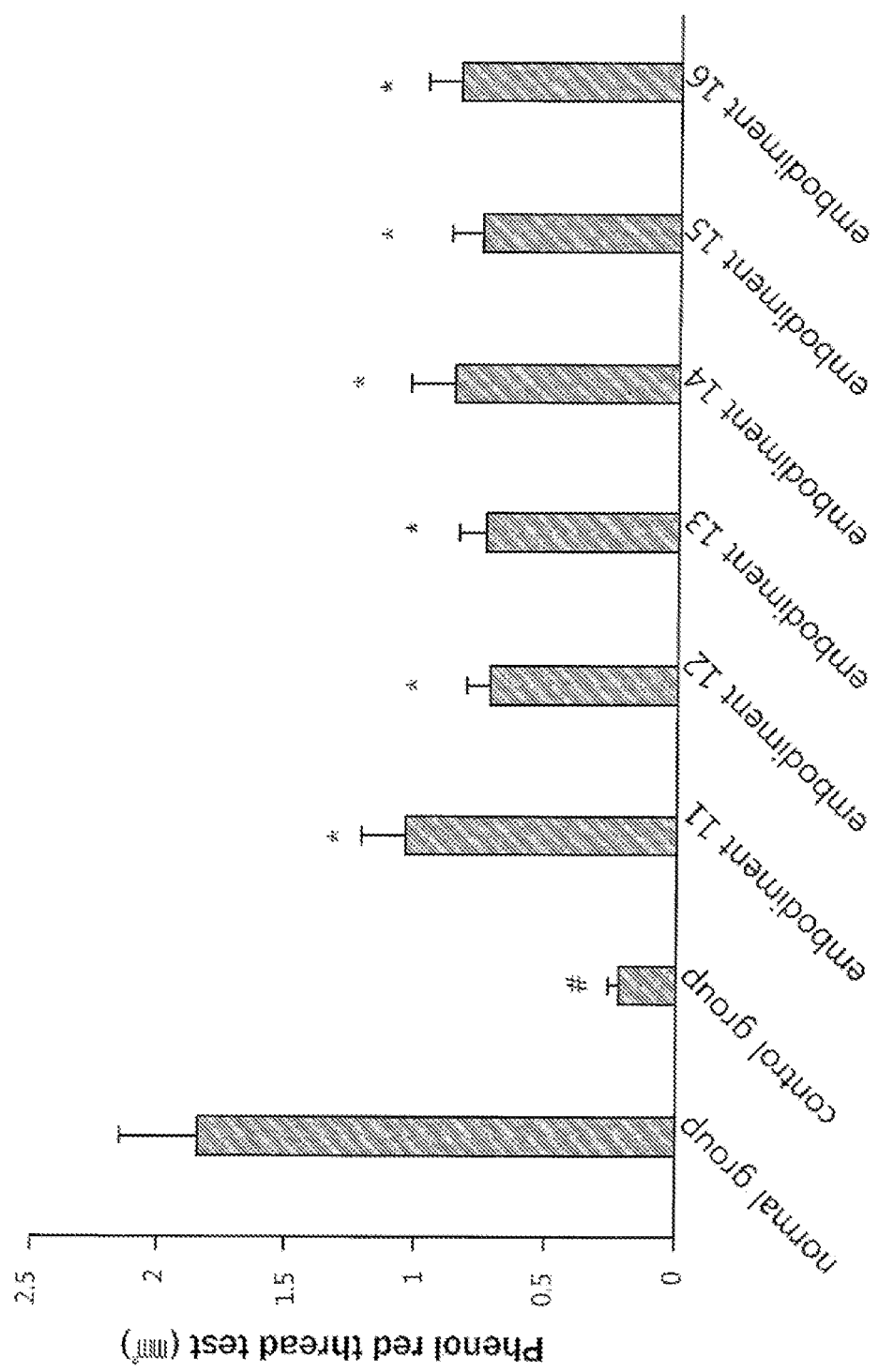
Figure 4:
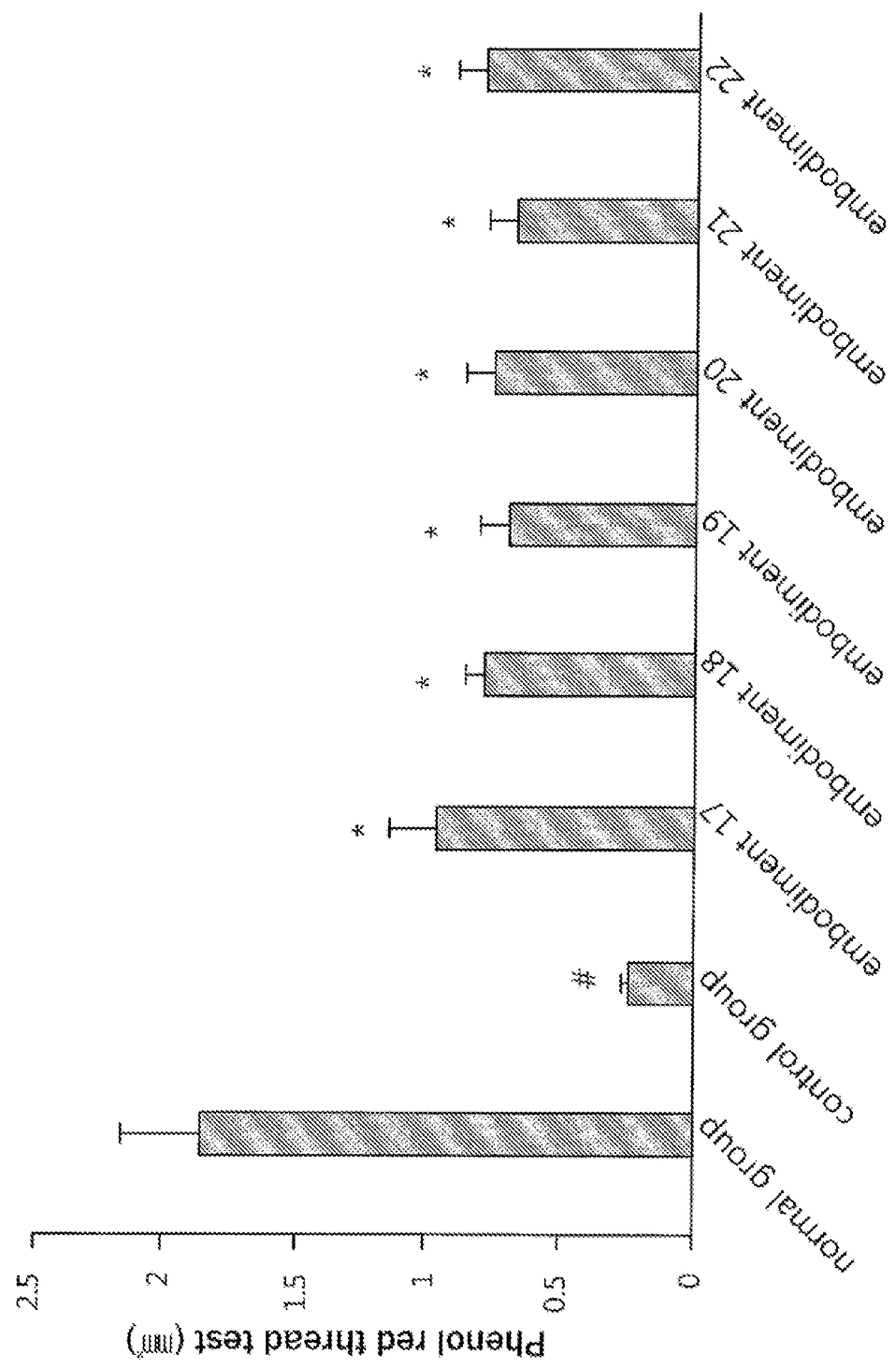
Figure 5:
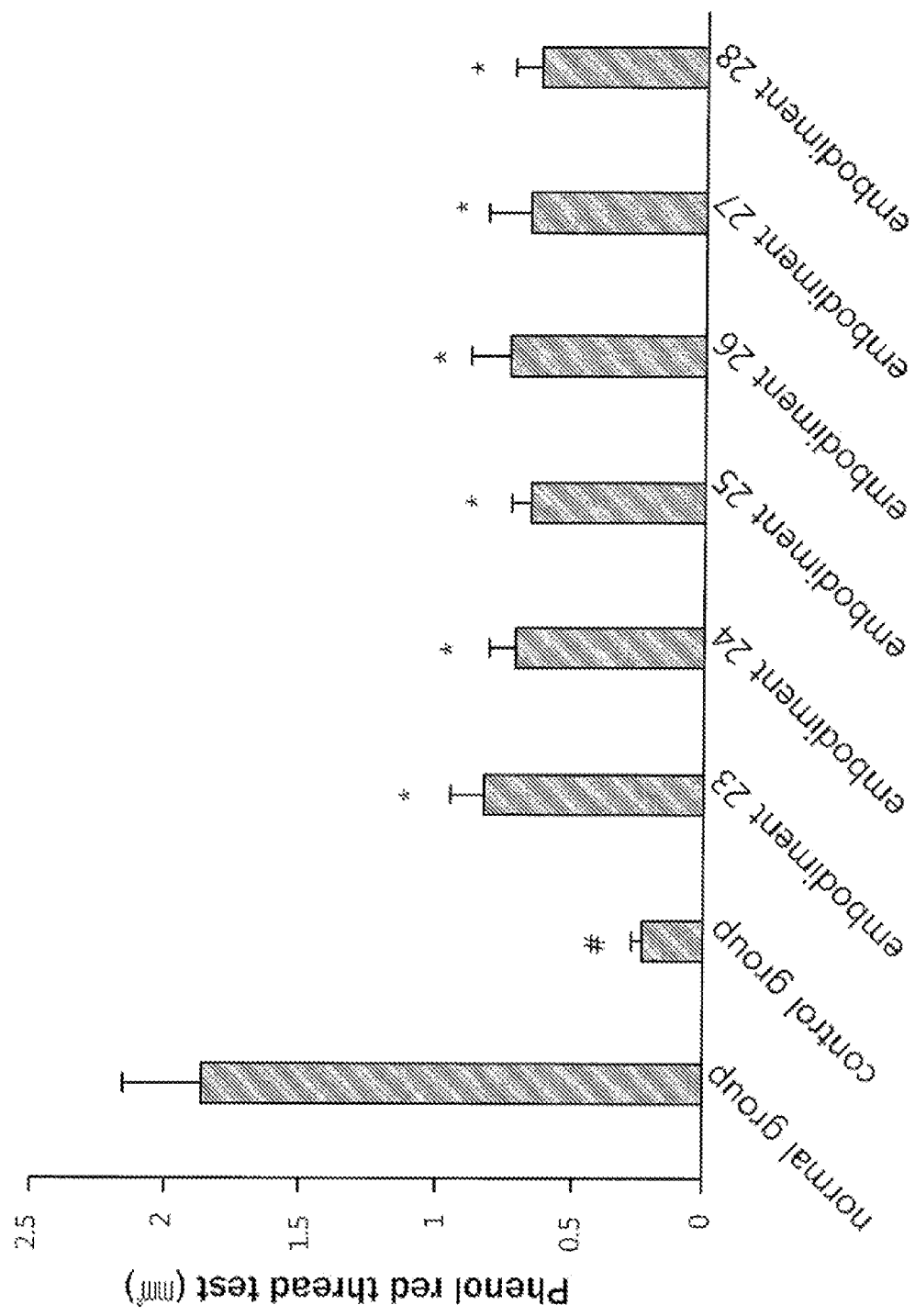
Figure 6:
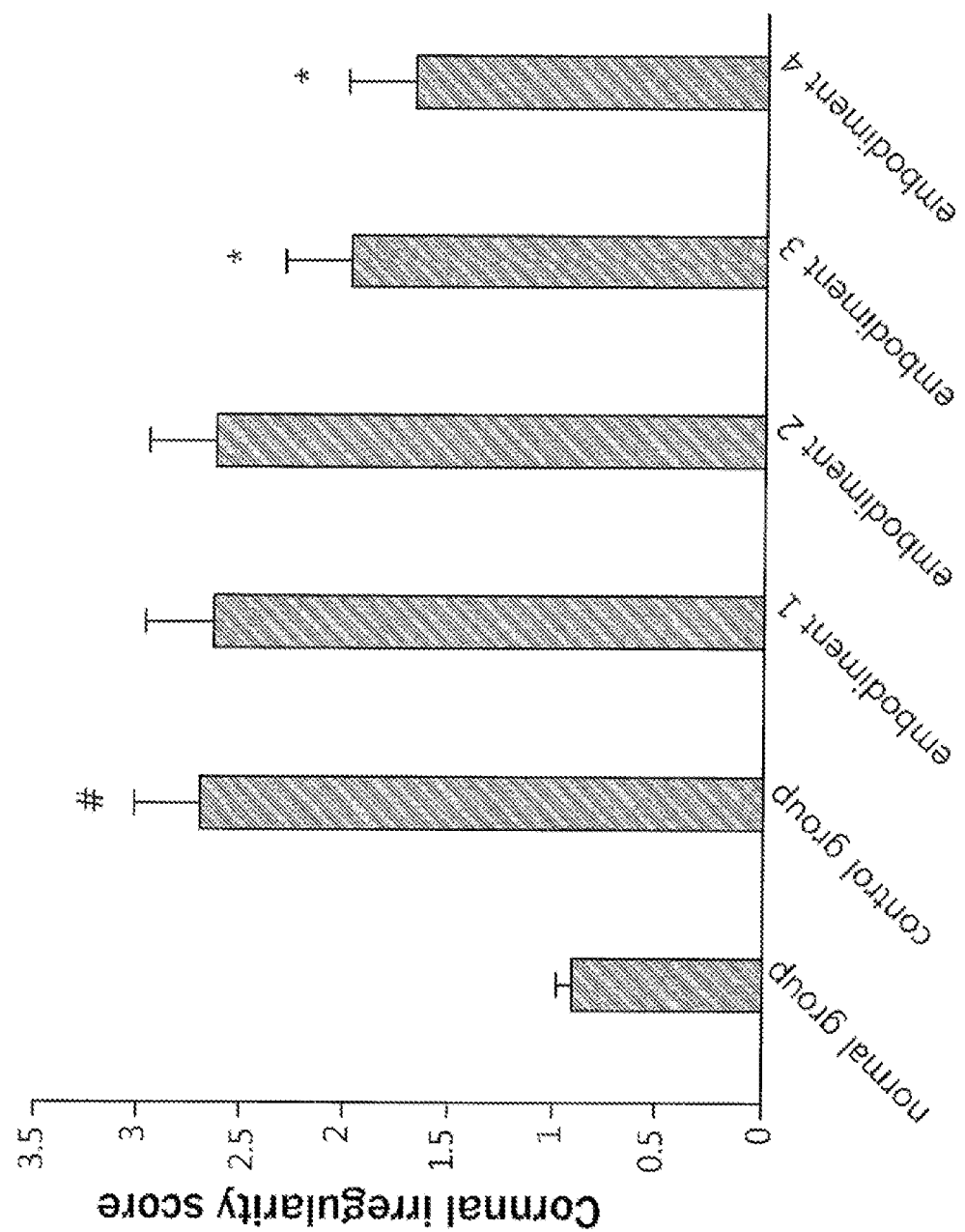
FIGS. 6 to 10 are graphs showing corneal smoothness in mouse models of dry eye syndrome at 10 days after administration of the oral compositions according to the present invention (Examples 1 to 28). In the graphs, "normal group" refers to mice with no dry eye syndrome induced, and "control group," to dry eye syndrome mouse models administered with vehicle only. Also, symbol "#" indicates $p<0.05$ against the normal group, and "*" indicates $p<0.05$ against the control group (t-test).
Figure 7:
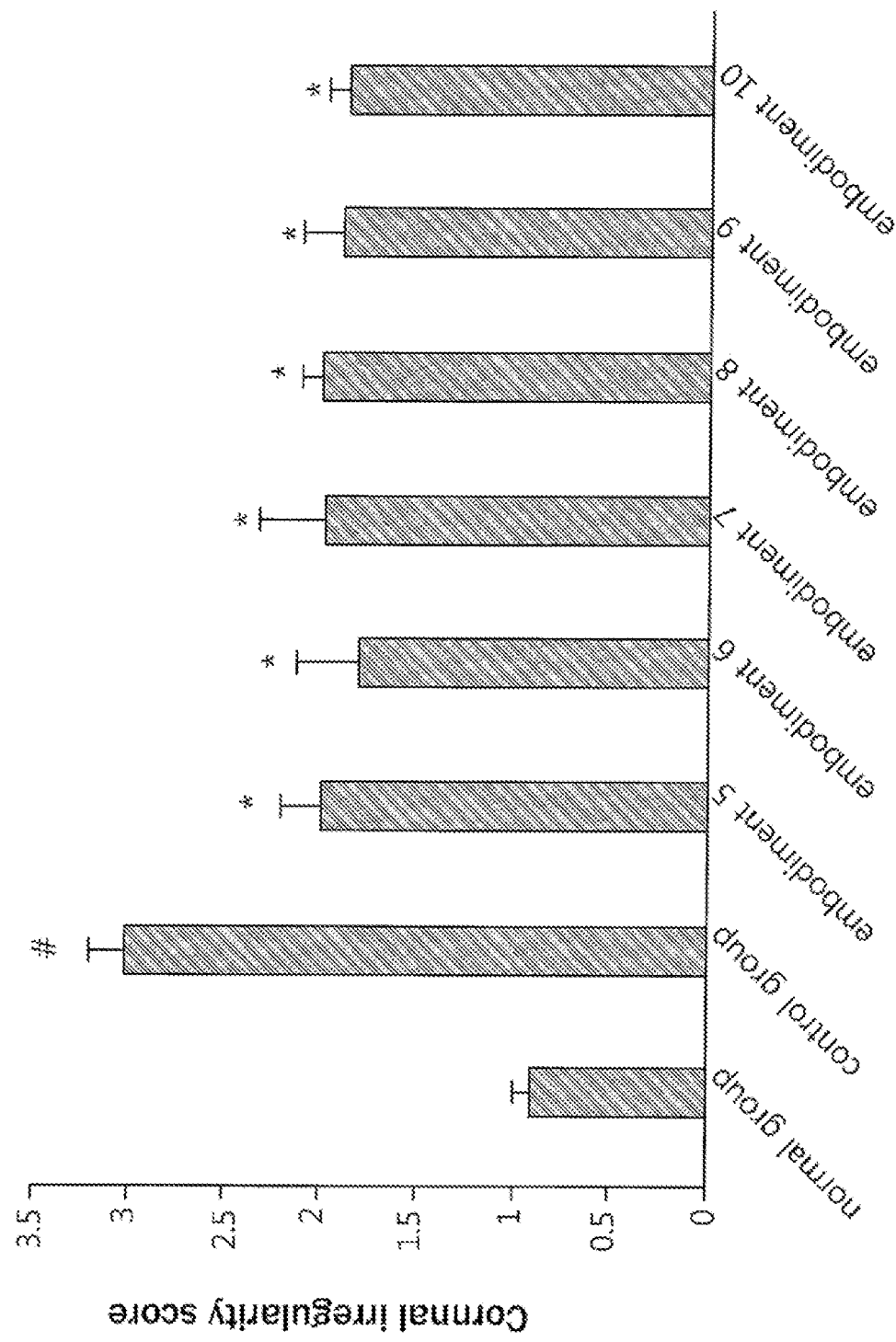
Figure 8:
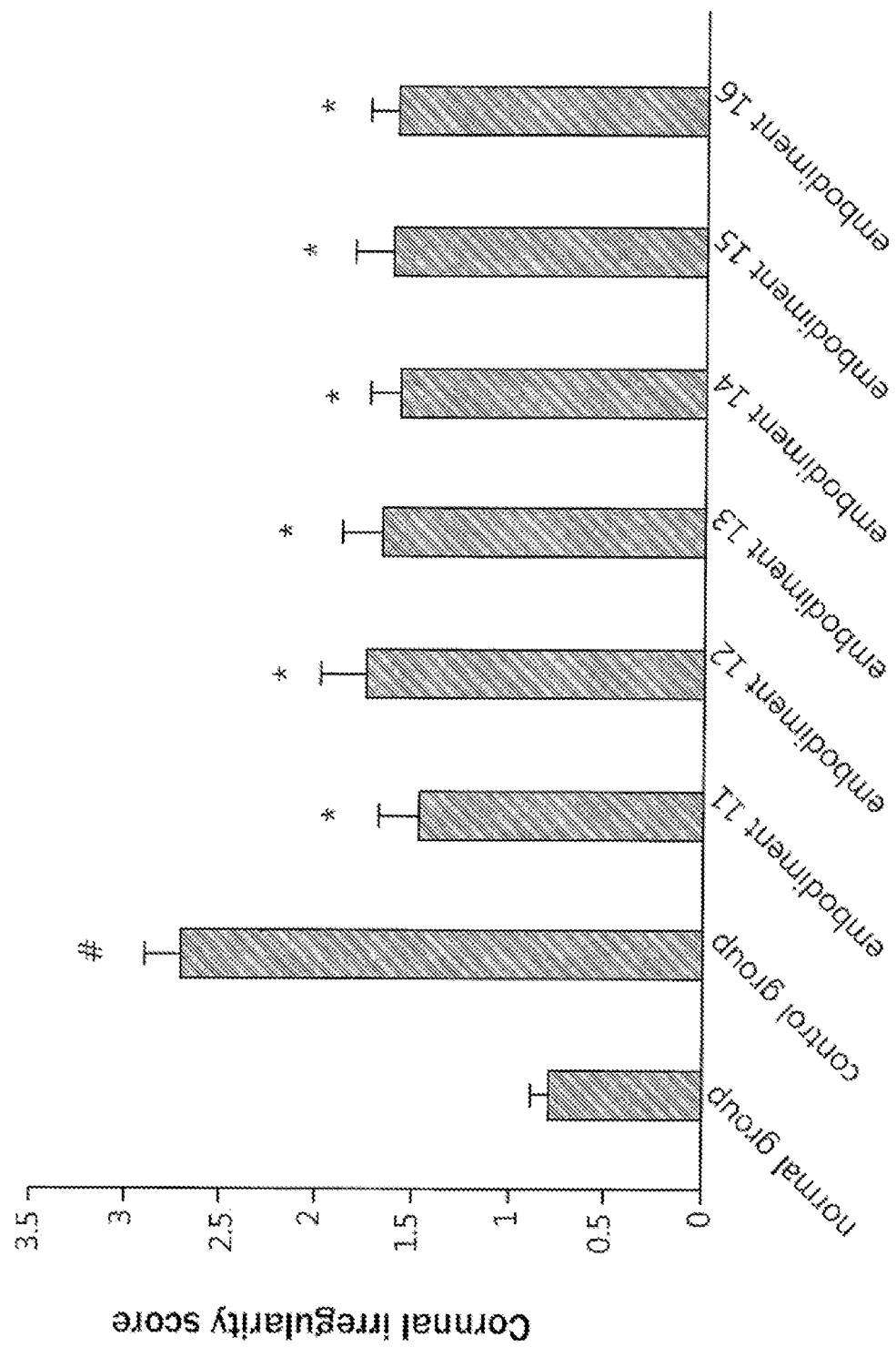
Figure 9:
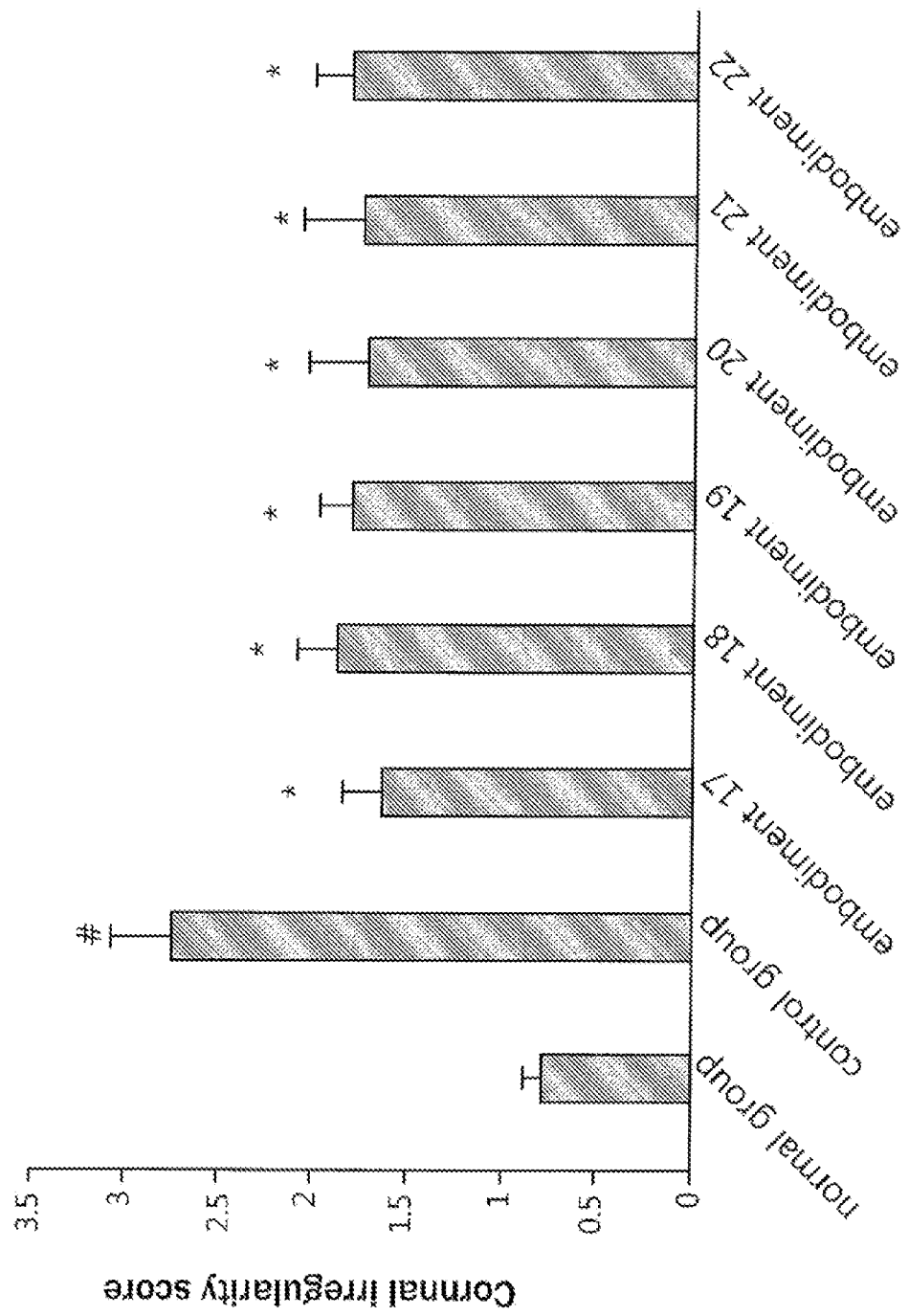
Figure 10:
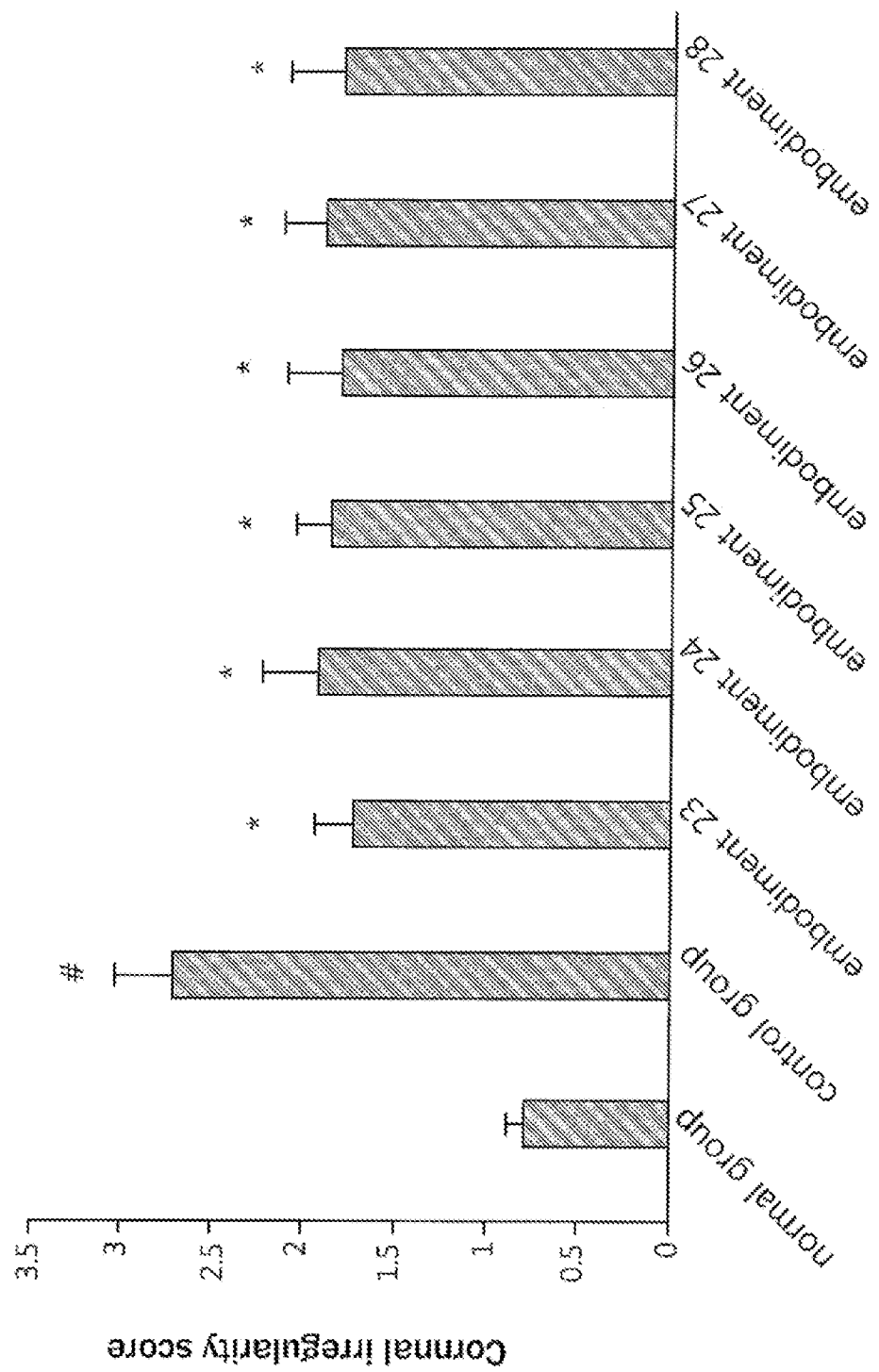
Figure 11:
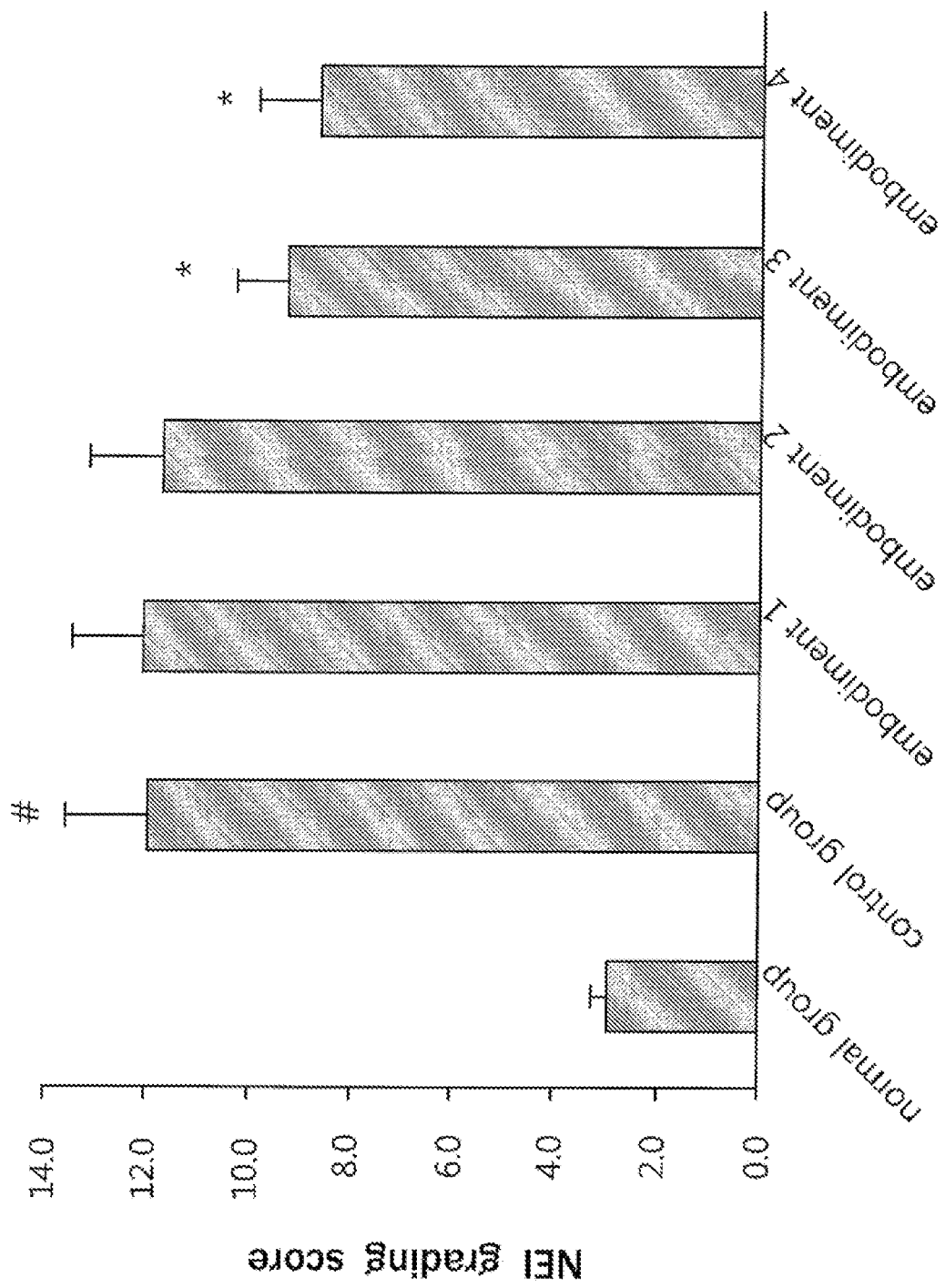
FIGS. 11 to 15 are graphs showing corneal permeability in mouse models of dry eye syndrome at 10 days after administration of the oral compositions according to the present invention (Examples 1 to 28). In the graphs, "normal group" refers to mice with no dry eye syndrome induced, and "control group," to dry eye syndrome mouse models administered with vehicle only. Also, symbol "#" indicates $p<0.05$ against the normal group, and "*" indicates $p<0.05$ against the control group (t-test).
Figure 12:
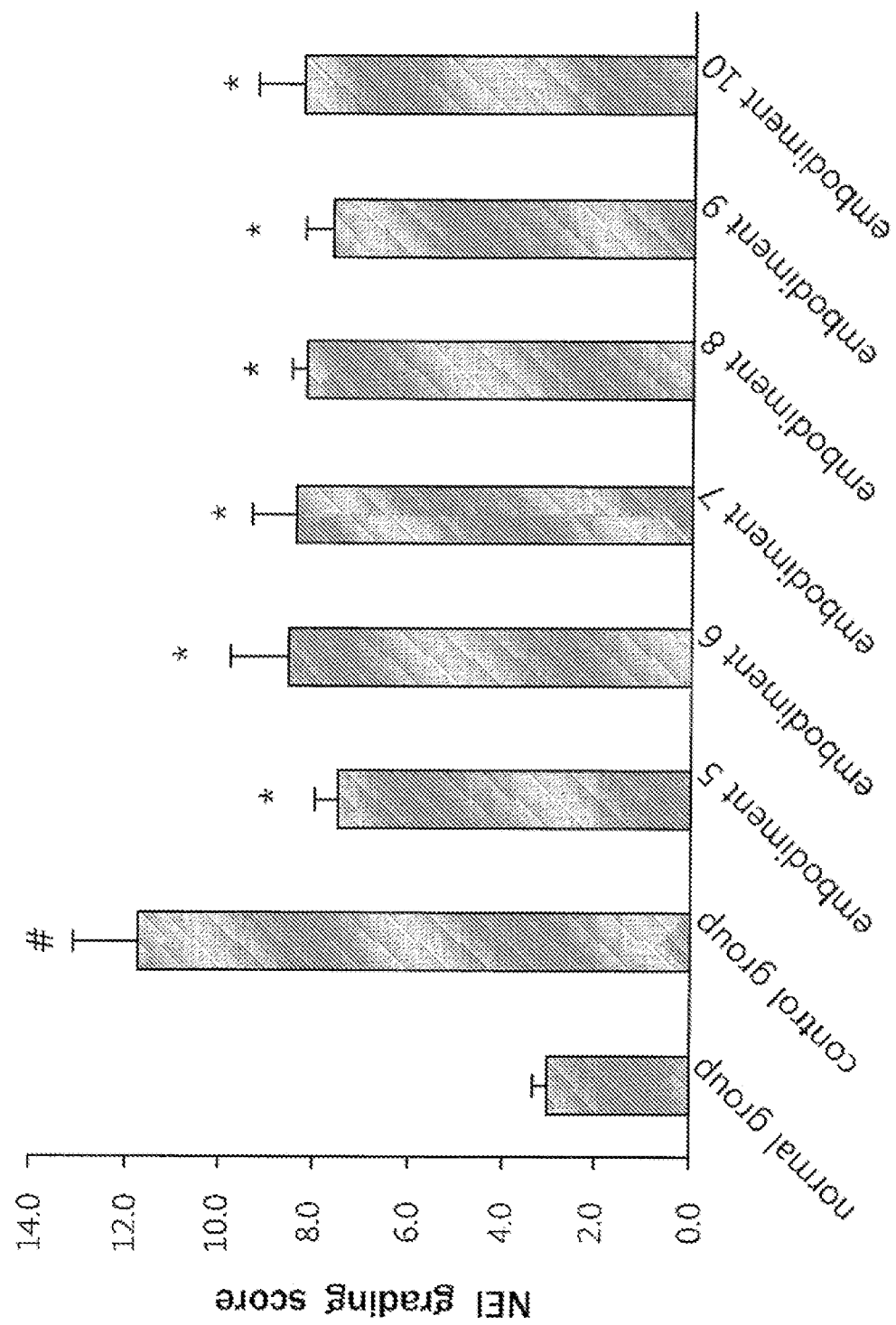
Figure 13:
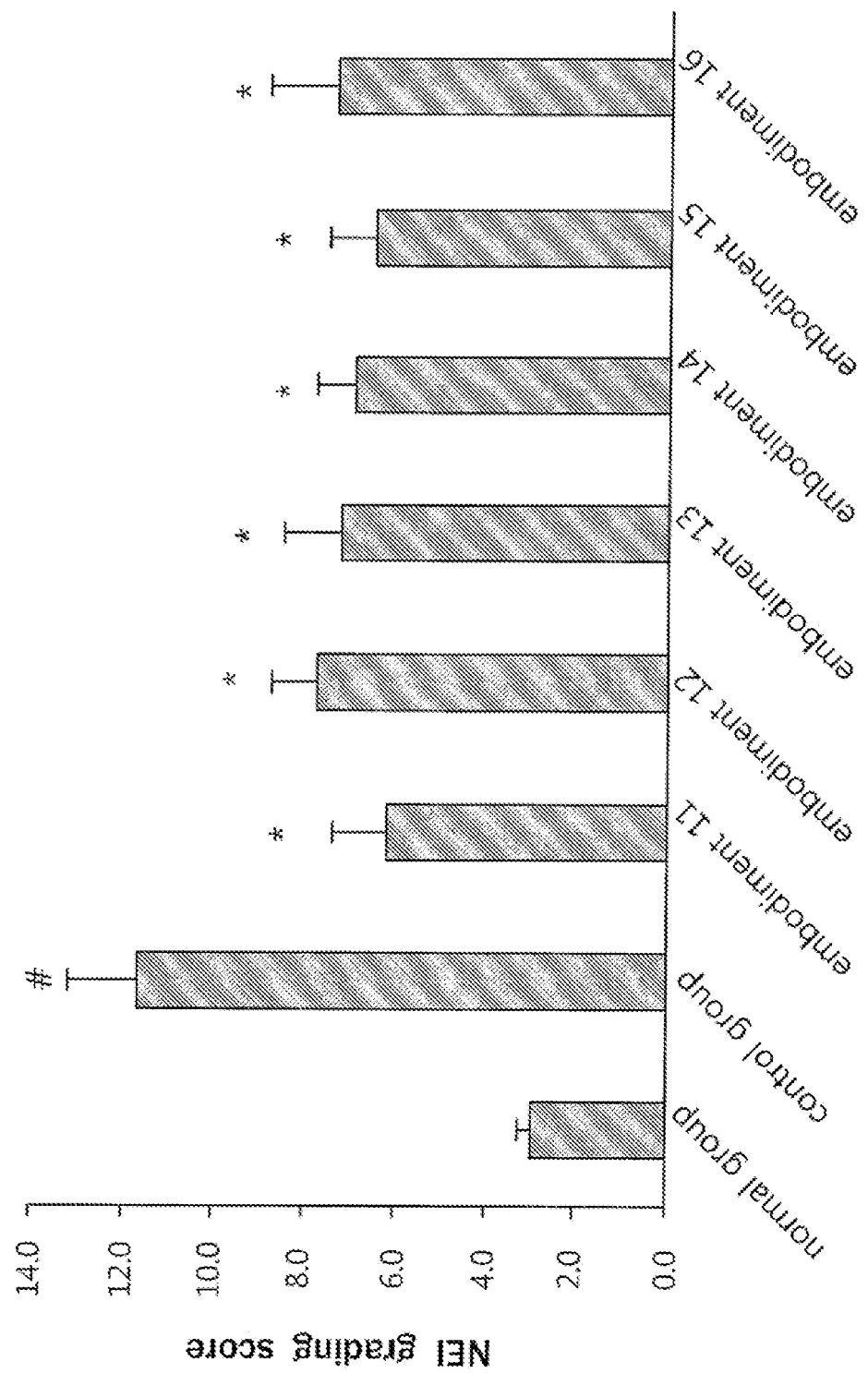
Figure 14:
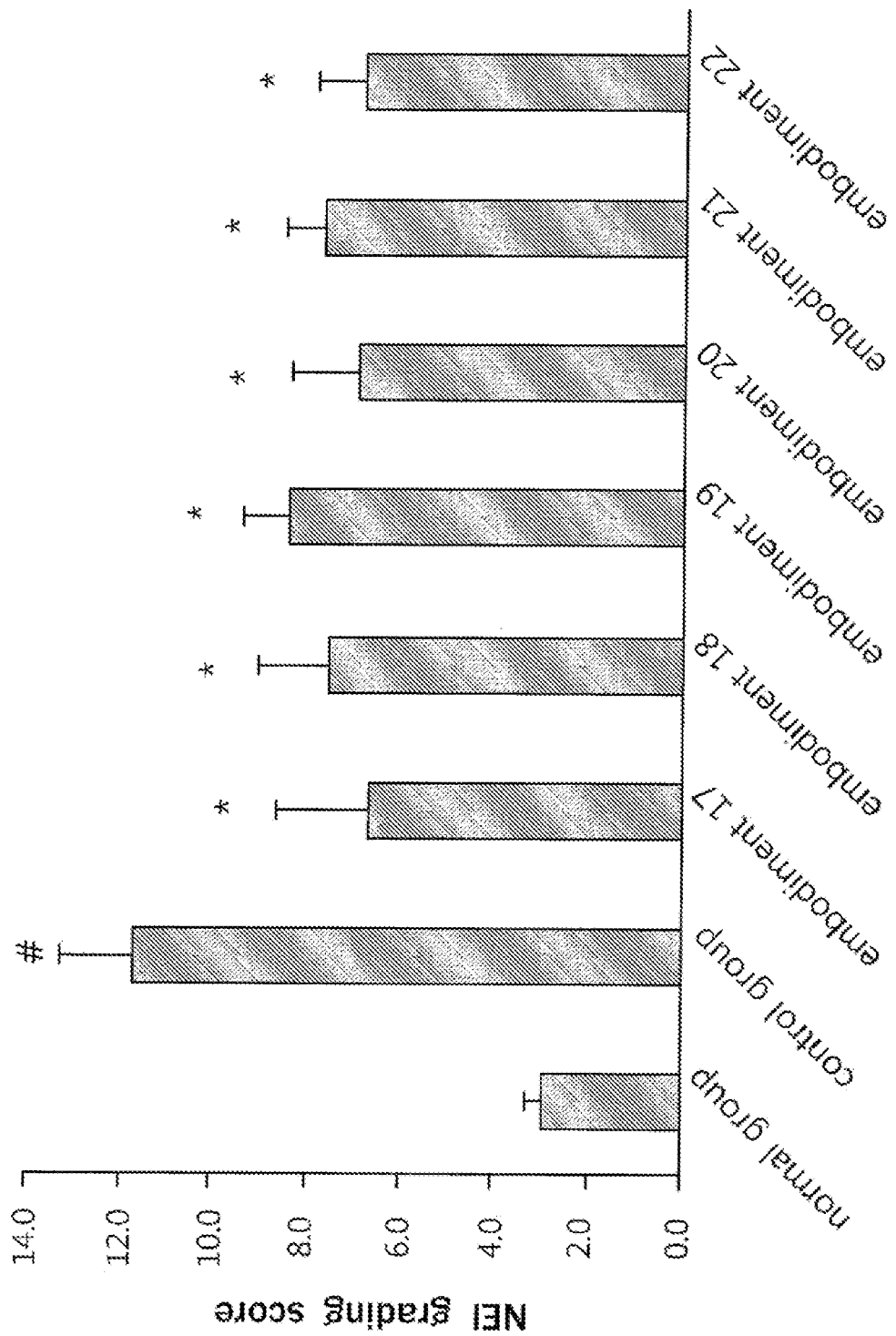
Figure 15:
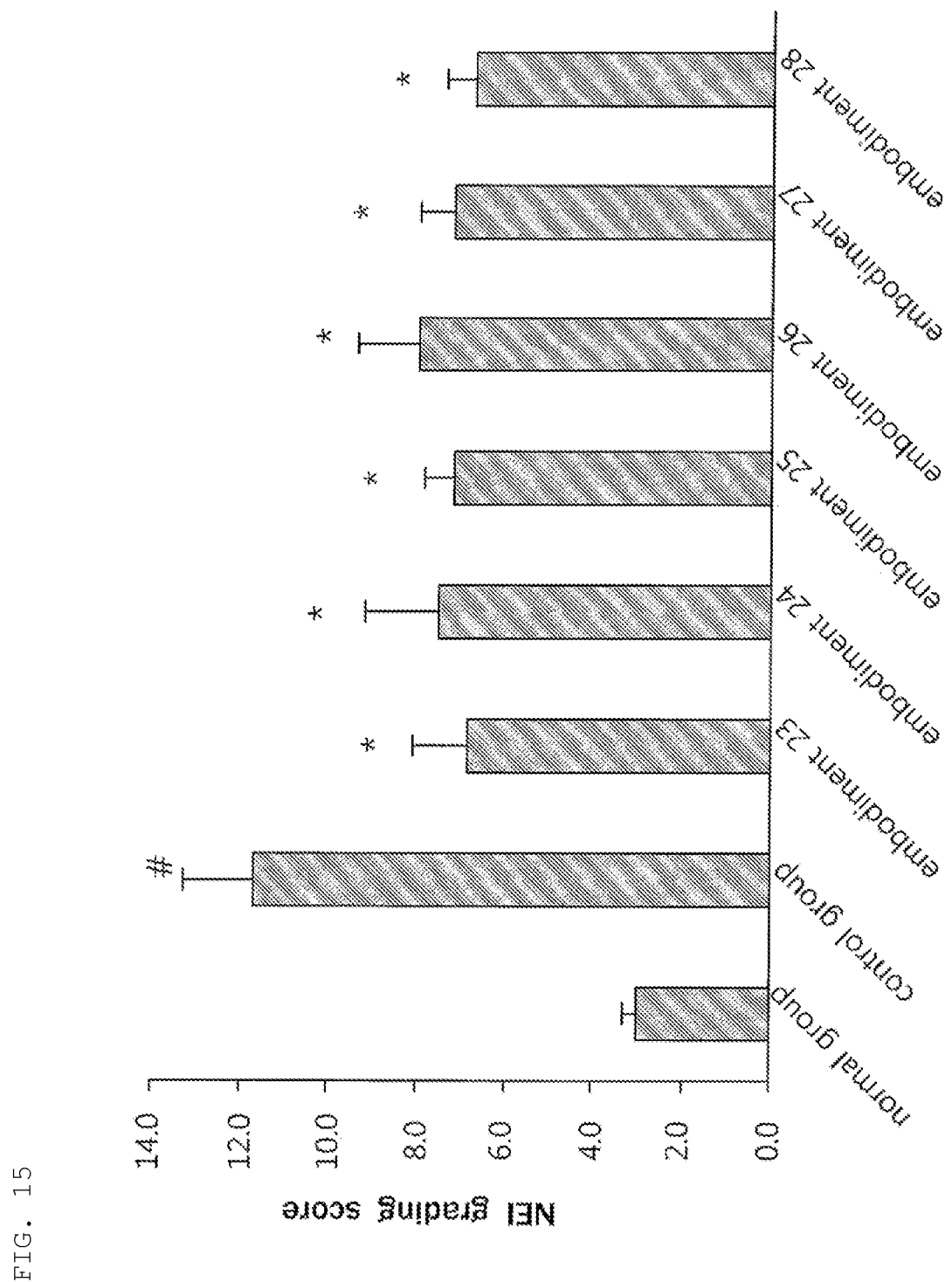

According to Experimental Examples of the present invention, the aforementioned prodrugs have superior therapeutic effects on dry eye syndrome compared to rebamipide (see FIGS. 1 to 15).

The pharmaceutically acceptable salt of the rebamipide prodrug employable in the composition of the present invention refers to an acid addition salt formed with an acid. Examples of the acid include, but are not limited to, hydrochloric acid, sulfuric acid, nitric acid, phosphoric acid, hydrobromic acid, hydroiodic acid, tartaric acid, formic acid, citric acid, acetic acid, trichloroacetic acid, trifluoroacetic acid, gluconic acid, benzoic acid, lactic acid, oxalic acid, fumaric acid, malonic acid, maleic acid, methanesulfonic acid, benzenesulfonic acid, p-toluenesulfonic acid, and naphthalenesulfonic acid. Preferred examples of the salt include an acid addition salt formed with sulfuric acid, malonic acid, or oxalic acid.

According to Experimental Examples of the present invention, the aforementioned prodrugs have superior therapeutic effects on dry eye syndrome compared to rebamipide (see FIGS. 1 to 15).

In the composition of the present invention, rebamipide or a prodrug thereof, or a pharmaceutically acceptable salt thereof may be used in an amount of 1 to 50% by weight, based on the total amount of the composition.

In addition, the pharmaceutical composition of the present invention may further comprise a pharmaceutically acceptable carrier or additive.

The expression "pharmaceutically acceptable," as used herein, refers to pertaining to being physiologically compatible and not causing a gastrointestinal disorder, an allergic response such as dizziness, or analogous responses after administration to humans. The additive may be any one of excipients, disintegrants, binders, lubricants, wetting agents, suspending agents, stabilizers, and the like. Examples of excipients include lactose, mannitol, isomalt, microcrystalline cellulose, silicified microcrystalline cellulose, powdered cellulose, and the like. Examples of disintegrants include low-substituted hydroxypropylcellulose, crospovidone, sodium starch glycolate, croscarmellose sodium, starch, and the like. Examples of binders include hydroxypropylcellulose, hypromellose, povidone, copovidone, pregelatinized starch, and the like. Examples of lubricants include stearic acid, magnesium stearate, sodium fumaryl stearate, and the like. Examples of wetting agents include polyoxyethylene sorbitan fatty acid esters, poloxamers, polyoxyethylene castor oil derivatives, and the like. Examples of suspending agents include hypromellose, hydroxypropylcellulose, povidone, copovidone, sodium carboxymethylcellulose, methylcellulose, and the like. Examples of stabilizers include citric acid, fumaric acid, succinic acid, and the like. Further, the pharmaceutical composition of the present invention may additionally comprise any one of anti-coagulants, flavoring agents, emulsifiers, preservatives, etc.

Moreover, the pharmaceutical composition of the present invention may be formulated by a known method in the art, to provide an immediate, sustained or delayed release of the active ingredient after administration to a mammal. The pharmaceutical formulation may be in the form of powders, granules, tablets, suspensions, emulsions, syrups, aerosols, or soft or hard gelatin capsules.

The pharmaceutically effective dose of rebamipide or a prodrug thereof, or a pharmaceutically acceptable salt thereof depends on the subject being treated, the severity of the disease or condition, the rate of administration, the judgment of the prescribing physician. The compound may be administered, via oral route, in a daily dosage of about 0.5 mg/kg body weight to 100 mg/kg body, and preferably about 0.5 mg/kg body weight to 5 mg/kg body weight. In some cases, less than the aforementioned minimum amount may be sufficient, while in other cases the upper limit must be exceeded, unless no noxious, adverse side effects occur. In the case of administration of greater amounts, it may be advisable to divide them into several individual doses over the day.

Furthermore, the present invention provides a method for preventing or treating dry eye syndrome in a subject in need thereof, the method comprising administrating to the subject rebamipide or a prodrug thereof, or a pharmaceutically acceptable salt thereof. The subject may be a subject suffering from or at risk of dry eye syndrome, for example, a mammal, preferably human.

In addition, the present invention provides a use of rebamipide or a prodrug thereof, or a pharmaceutically acceptable salt thereof in the preparation of a medicament for preventing or treating dry eye syndrome.

A better understanding of the present invention may be obtained through the following examples which are set forth to illustrate, but are not to be construed as limiting the present invention.

Examples 1 to 4

Preparation of Oral Agents Containing Rebamipide

Polysorbate 80 (Fluka) 3.0 g as a dispersant was dissolved in 100 mL of purified water to prepare a vehicle for suspension of a drug. 1, 2, 4 and 6 g of rebamipide (Chemical Formula I; Hanseo chem Co. Ltd.) were each added thereto, followed by stirring the mixture for 10 minutes to prepare suspensions (Examples 1 to 4). The suspensions (5 mL/kg) were administered twice a day to dry eye syndrome models of 8-week old male C57BL/6 mice according to the doses listed in Table 1.

Examples 5 to 10

Preparation of Oral Agents Containing Rebamipide

Citric acid (Sigma-Aldrich) 0.1 g as a stabilizer and hypromellose 2910 (Pharmacoat 615, Shin-etsu) 2 g as a suspending agent were dissolved in 100 mL of purified water to prepare a vehicle for suspension of a drug. Ig of rebamipide prodrugs I to VI (Chemical Formulae II to VII; Samjin Pharmaceutical Co. Ltd.) were each added thereto, followed by stirring the mixture for 10 minutes to prepare suspensions (Examples 5 to 10). The suspensions (5 mL/kg) were administered twice a day to dry eye syndrome models of 8-week old male C57BL/6 mice according to the doses listed in Table 1.

Examples 11 to 16

Preparation of Oral Agents Containing Rebamipide Prodrug Malonates

The procedures of Examples 5 to 10 were repeated, except for using malonates thereof (Samjin Pharmaceutical Co. Ltd.) in an amount equivalent to 1 g based on each prodrug, instead of rebamipide prodrugs I to VI, to prepare suspensions (Examples 11 to 16). The suspensions (5 mL/kg) were administered twice a day to dry eye syndrome models of 8-week old male C57BL/6 mice according to the doses listed in Table 1.

Examples 17 to 22

Preparation of Oral Agents Containing Rebamipide Prodrug Oxalates

The procedures of Examples 5 to 10 were repeated, except for using oxalates thereof (Samjin Pharmaceutical Co. Ltd.) in an amount equivalent to 1 g based on each prodrug, instead of rebamipide prodrugs I to VI, to prepare suspensions (Examples 17 to 22). The suspensions (5 mL/kg) were administered twice a day to dry eye syndrome models of 8-week old male C57BL/6 mice according to the doses listed in Table 1.

Examples 23 to 28

Preparation of Oral Agents Containing Rebamipide Prodrug Sulfates

The procedures of Examples 5 to 9 were repeated, except for using sulfates thereof (Samjin Pharmaceutical Co. Ltd.) in an amount equivalent to 1 g based on each prodrug, instead of rebamipide prodrugs I to VI, to prepare suspensions (Examples 23 to 28). The suspensions (5 mL/kg) were administered twice a day to dry eye syndrome models of 8-week old male C57BL/6 mice according to the doses listed in Table 1.

TABLE 1

| Example | Drug | Dose |
|---|---|---|
| 1 | Rebamipide | 50 mg/kg |
| 2 | Rebamipide | 100 mg/kg |
| 3 | Rebamipide | 200 mg/kg |
| 4 | Rebamipide | 300 mg/kg |
| 5 | Rebamipide prodrug I | 50 mg/kg |
| 6 | Rebamipide prodrug II | 50 mg/kg |
| 7 | Rebamipide prodrug III | 50 mg/kg |
| 8 | Rebamipide prodrug IV | 50 mg/kg* |
| 9 | Rebamipide prodrug V | 50 mg/kg* |
| 10 | Rebamipide prodrug VI | 50 mg/kg* |
| 11 | Rebamipide prodrug I malonate | 50 mg/kg* |
| 12 | Rebamipide prodrug II malonate | 50 mg/kg* |
| 13 | Rebamipide prodrug III malonate | 50 mg/kg* |
| 14 | Rebamipide prodrug IV malonate | 50 mg/kg* |
| 15 | Rebamipide prodrug V malonate | 50 mg/kg* |
| 16 | Rebamipide prodrug VI malonate | 50 mg/kg* |
| 17 | Rebamipide prodrug I oxalate | 50 mg/kg* |
| 18 | Rebamipide prodrug II oxalate | 50 mg/kg* |
| 19 | Rebamipide prodrug III oxalate | 50 mg/kg* |
| 20 | Rebamipide prodrug IV oxalate | 50 mg/kg* |
| 21 | Rebamipide prodrug V oxalate | 50 mg/kg* |
| 22 | Rebamipide prodrug VI oxalate | 50 mg/kg* |
| 23 | Rebamipide prodrug I sulfate | 50 mg/kg* |
| 24 | Rebamipide prodrug II sulfate | 50 mg/kg* |
| 25 | Rebamipide prodrug III sulfate | 50 mg/kg* |
| 26 | Rebamipide prodrug IV sulfate | 50 mg/kg* |
| 27 | Rebamipide prodrug V sulfate | 50 mg/kg* |
| 28 | Rebamipide prodrug VI sulfate | 50 mg/kg* |

*The above doses are based on rebamipide prodrug.

Experimental Example 1: Efficacy Analysis of Drugs Using an Animal Model of Dry Eye Syndrome <1-1> Construction of an Animal Model of Dry Eye Syndrome Eight-week old male C57BL/6 mice (Charles River laboratories) were quarantined for one week and divided into several groups of eight animals evenly according to their average body weight and standard deviation.

For experimental groups (administered with Examples 1 to 28), dry eye syndrome was induced by subcutaneous injection of scopolamine (2.5 mg/mL, Sigma-Aldrich) for 10 days with exposure to air draft (25-40% relative humidity) for 18 hours per day. Then, mice were orally administered with the suspensions of Examples 1 to 29, twice a day for total 10 days, respectively.

Meanwhile, for a normal group, neither the drug nor the vehicle was administered to normal mice. And, for a control group, the vehicle was administered to the mice with dry eye syndrome.

<1-2> Measurement of Tear Production Volume

Ten (10) days after administration of the drugs, the control group and experimental groups were analyzed for tear production volume. Tear production volume was measured by placing phenol red cotton threads in the lateral canthus of the eye of the mice, holding it in place for a certain period of time, and analyzing the wet area (mm$^2$) using an Image-Inside program (Ver 2.32). The measurement results were shown in FIGS. 1 to 5.

As shown in FIGS. 1 to 5, rebamipide at dosages of 200 mg/kg or more (Examples 3 and 4) showed significant increases in tear production volume, compared to the control group. In addition, rebamipide prodrugs and salts thereof (Examples 5 to 28) also exhibited significant increases in tear production volume compared to the control group.

<1-3> Analysis of Corneal Smoothness

In order to analyze corneal smoothness, each mouse was euthanized at 10 days after administration of the drugs. Then, the corneal surface of each mouse was observed under a stereoscopic zoom microscope (Nikon), and was scored based on the corneal irregularity (four-point scale, 0.5: normal, 1: minimal, 1.5: mild, 3: moderate, 4: severe). The scores from two experts were averaged. The results were shown in FIGS. 6 to 10.

As shown in FIGS. 6 to 10, rebamipide at dosages of 200 mg/kg or more (Examples 3 and 4) showed a significant improvement in corneal smoothness, compared to the control group. In addition, rebamipide prodrugs and salts thereof (Examples 5 to 28) also exhibited significant improvements in corneal smoothness compared to the control group.

<1-4> Corneal Epithelial Cell Damages

In order to evaluate the degree of corneal epithelial cell damages, 5 μL of the solution containing 1% fluorescein sodium salt (Sigma-Aldrich) as a fluorescent dye in balanced salt solution, was dropped into the conjunctival sac of the mice. The eyes of the mice were closed for at least one hour using an adhesive tape. The eyes were rinsed with distilled water to remove excess unpenetrated fluorescent dyes. Then, the eyes were enucleated, analyzed for the level of green fluorescence, and the images were taken. The images were analyzed using an ImageJ 1.38x program (http://rsb.info.nih.gov, NIH, Baltimore, USA) to calculate green fluorescence intensity. Damage to corneal epithelial cell was scored as follows: 3: normal, 6: minimal, 9: mild, 12: moderate, and 15: severe.

As shown in FIGS. 11 to 15, rebamipide at dosages of 200 mg/kg or more (Examples 3 and 4) showed a significant reduction in corneal permeability of fluorescent dye, compared to the control group. In addition, rebamipide prodrugs and salts thereof (Examples 5 to 28) also exhibited significant reductions in corneal permeability of fluorescent dye compared to the control group.

The invention claimed is:

1. An oral pharmaceutical composition, comprising a pharmaceutically acceptable salt of a prodrug of rebamipide, as an active ingredient,
wherein the prodrug of rebamipide is 2-morpholinoethyl 2-(4-chlorobenzamido)-3-(2-oxo-1,2-dihydroquinolin-4-yl)propanoate represented by Chemical Formulae II, and
wherein the pharmaceutically acceptable salt is a sulfate of a prodrug of rebamipide, a malonate of a prodrug of rebamipide, or an oxalate of a prodrug of rebamipide:

[Chemical Formula II]

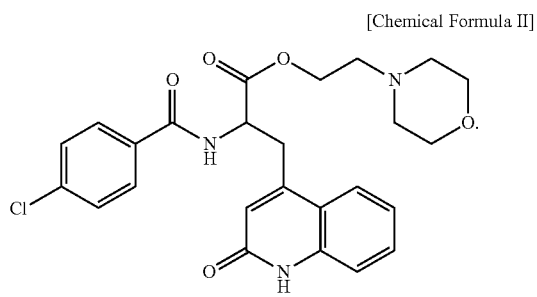 [SMILES: O=C(NC(Cc1cc(=O)[nH]c2ccccc12)C(=O)OCCN1CCOCC1)c1ccc(Cl)cc1]

2. The oral pharmaceutical composition of claim 1, wherein the sulfate, the malonate or the oxalate of the prodrug of rebamipide is used in an amount of 1 to 50% by weight, based on the total amount of the composition.

3. The oral pharmaceutical composition of claim 1, which further comprises a pharmaceutically acceptable carrier or additive.

4. The oral pharmaceutical composition of claim 3, wherein the pharmaceutically acceptable additive is selected from the group consisting of excipients, disintegrants, binders, lubricants, wetting agents, suspending agents, stabilizers, and a mixture thereof.

5. The oral pharmaceutical composition of claim 1, wherein a formulation of the pharmaceutical composition is selected from the group consisting of powders, granules, tablets, suspensions, emulsions, syrups, aerosols, and soft or hard gelatin capsules.

6. The oral pharmaceutical composition of claim 1, wherein the prodrug of rebamipide, or the pharmaceutically acceptable salt thereof is used in an amount of 1 to 50% by weight, based on the total amount of the composition.

7. A method of preventing or treating dry eye syndrome in a subject in need thereof, comprising:
  providing the oral pharmaceutical composition of claim 1; and
  administering the pharmaceutical composition orally to the subject.

8. The method of claim 7, wherein the sulfate, the malonate or the oxalate of the prodrug of rebamipide, or the pharmaceutically acceptable salt thereof is used in an amount of 1 to 50% by weight, based on the total amount of the composition.

9. The method of claim 7, which further comprises a pharmaceutically acceptable carrier or additive.

10. The method of claim 9, wherein the pharmaceutically acceptable additive is selected from the group consisting of excipients, disintegrants, binders, lubricants, wetting agents, suspending agents, stabilizers, and a mixture thereof.

11. The method of claim 7, wherein a formulation of the pharmaceutical composition is selected from the group consisting of powders, granules, tablets, suspensions, emulsions, syrups, aerosols, and soft or hard gelatin capsules.

* * * * *